United States Patent [19]

Champseix et al.

[11] Patent Number: 4,928,539
[45] Date of Patent: May 29, 1990

[54] DEVICE FOR AUTOMATICALLY TAKING LIQUID FROM A BOTTLE

[75] Inventors: Henri Champseix, Montesson; Serge Champseix, Les Mureaux, both of France

[73] Assignee: A.B.X., Hauts-de-Seine, France

[21] Appl. No.: 104,101

[22] Filed: Oct. 5, 1987

[30] Foreign Application Priority Data

Oct. 6, 1986 [FR] France ................. 86 13875

[51] Int. Cl.$^5$ .................. G01N 35/00; G01N 1/10; G01N 35/06
[52] U.S. Cl. ................. 73/864.24; 73/863.85; 73/864.22; 422/64
[58] Field of Search .......... 73/864.24, 864.22, 864.85, 73/863.85, 864.25, 864.21, 864.86, 864.82; 422/63, 64; 436/47, 49, 54; 222/82, 83, 83.5; 83/919

[56] References Cited

U.S. PATENT DOCUMENTS

| | | | |
|---|---|---|---|
| 3,266,322 | 8/1966 | Nagersmith et al. | 73/864.22 |
| 3,469,438 | 9/1969 | Gaumer | 73/864.24 X |
| 3,614,434 | 10/1971 | Horwitz et al. | 73/864.24 X |
| 3,788,177 | 1/1974 | Williamson | 83/454 |
| 4,094,197 | 6/1978 | Harris, Sr. et al. | 73/863.81 |
| 4,387,076 | 6/1983 | Cobrera et al. | 73/864.82 X |
| 4,472,352 | 9/1984 | Quesneau et al. | 422/64 X |
| 4,609,017 | 9/1986 | Coulter et al. | 73/864.24 X |
| 4,624,148 | 11/1986 | Averette | 73/864.21 |
| 4,669,321 | 6/1987 | Meyer | 73/863.85 |
| 4,688,436 | 8/1987 | Richon et al. | 73/864.81 |
| 4,817,443 | 4/1989 | Champseix et al. | 141/91 X |

FOREIGN PATENT DOCUMENTS

| | | |
|---|---|---|
| 0061317 | 9/1982 | European Pat. Off. . |
| 2326244 | 12/1974 | Fed. Rep. of Germany . |
| 2136707 | 12/1972 | France . |
| 2514504 | 4/1983 | France . |
| 1391692 | 4/1975 | United Kingdom . |
| 2075672 | 11/1981 | United Kingdom ............. 73/864.22 |

*Primary Examiner*—Tom Noland
*Attorney, Agent, or Firm*—Fleit, Jacobson, Cohn, Price, Holman & Stern

[57] ABSTRACT

A device is provided for automatically taking liquid from a bottle, including a stopper piercing assembly with a mobile block serving as support for a sample taking needle which moves vertically along guide columns under the action of a cylinder, a rinsing receptacle being fixedly mounted on the guide columns and traversed by the needle.

16 Claims, 2 Drawing Sheets

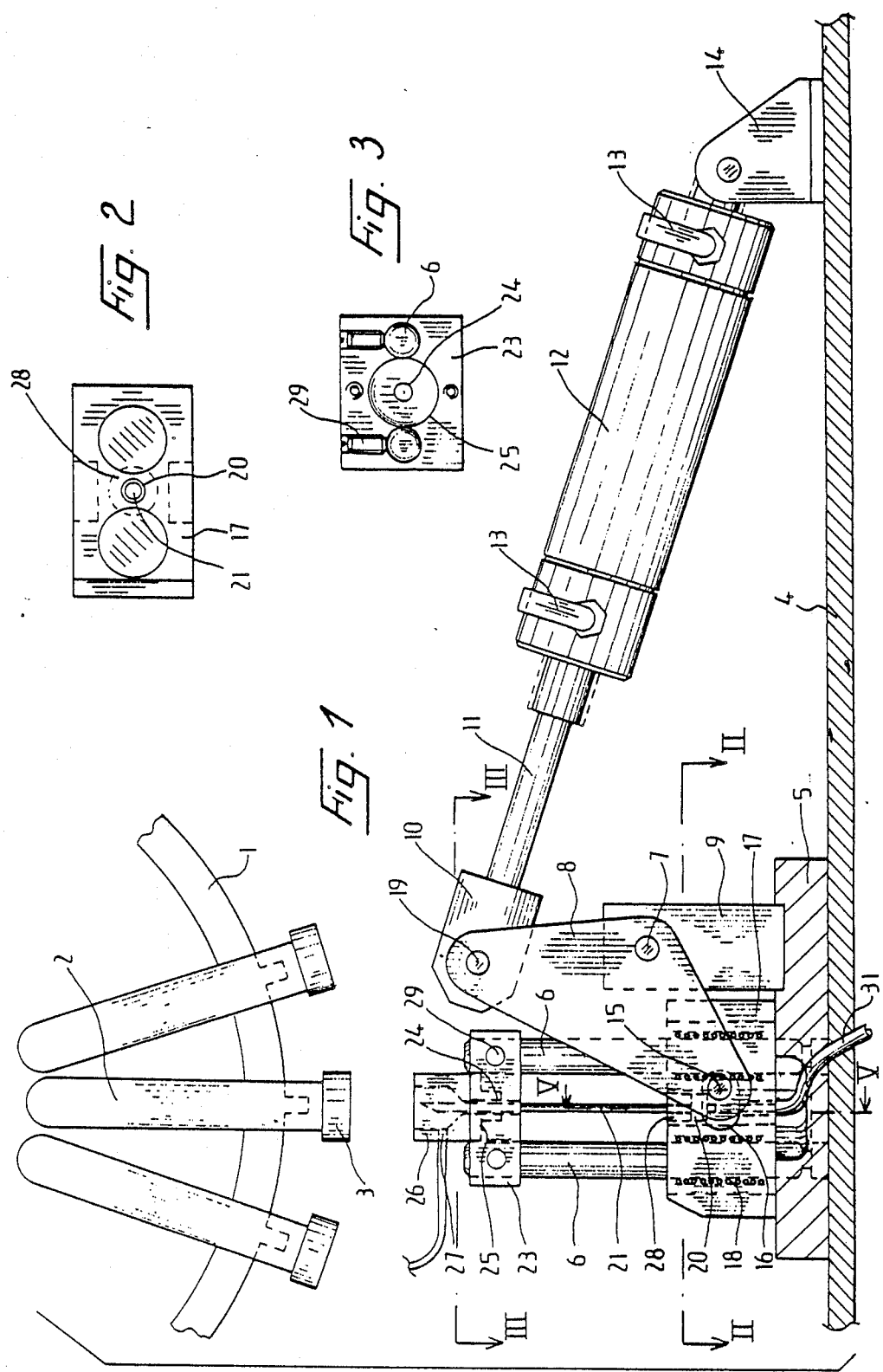

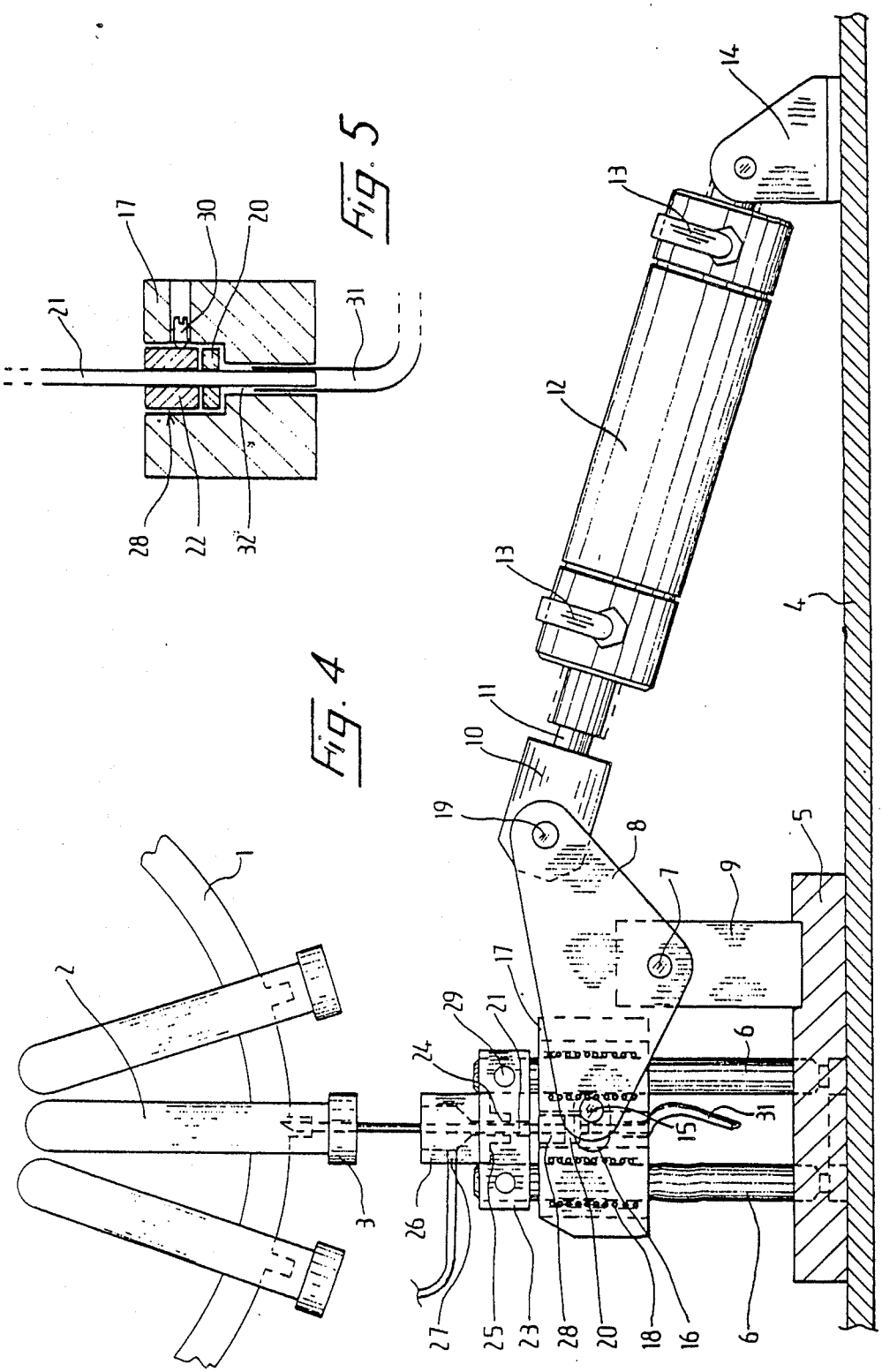

DEVICE FOR AUTOMATICALLY TAKING LIQUID FROM A BOTTLE

BACKGROUND OF THE INVENTION

1. Field of the Invention

The invention relates to a device for automatically taking liquid from a bottle and more precisely a tube plug piercing assembly for taking blood samples.

In medical biology analysis laboratories there now exist compact one piece automatic devices for counting elements representative of the peripheral blood from a whole blood sample. These automatic devices determine automatically a number of parameters such as white blood corpuscles and red blood corpuscles, the amount of hemoglobin, etc . . . For that, the blood samples must be transferred from a sample taking tube to the inside of the apparatus where they are subjected to appropriate measurements. For this, a needle is plunged into the tube and sucks up the desired amount of blood. This needle must then be carefully rinsed, inside and outside before the next measurement. Certain types of automatic devices are known which are provided with a fixed needle, connected to a suction system; the user then places the blood bottle under the needle and controls the sample taking cycle. Then after releasing and restoppering the bottle manually, he must rinse the needle.

These operations, which must be carried out with the greatest care, are fairly delicate, they require the permanent presence of the operator and are not very rapid. Furthermore, since the bottle and the tube from which the sample is taken is in a normal position, with its opening directed upwardly, the end of the needle must be able to penetrate to the bottom of the bottle so as to suck up the last few millimeters of blood. That means that the needle may dip into the blood over a great part of its height, which then requires more thorough rinsing. In addition, it is difficult to place the end of the needle at the bottom of a bottle without knocking against it with the risk of breaking the needle. For these multiple reasons, a more automatized sample taking system has been sought which improves the rates and avoids the above mentioned drawbacks.

2. Description of the Prior Art

Thus the necessity has been recognized of using needles handled automatically which take the blood from a tube. This latter comes into position on request opposite said needle, after being located in a storage support formed for example by a transversally movable carriage or a roundabout. The system is also known which consists in automatically taking the liquid from an upturned tube by means of a needle which passes through the stopper of a tube, this latter being made from a sufficiently flexible material to remain sealed after, the needle has been withdrawn, such as described in EP-A 0061317 and FR-A 25 14504. Thus, it is only possible to cause the needle to penetrate into the blood over a small part of its height and in addition to collect the last millimeters of blood remaining in the tube.

In order that such handling be ensured rapidly under the best hygenic conditions, the stoppers of the tubes must therefore be pierced automatically and reliably by means of a device which is readily associated with the automatic counting devices for which they form an efficient auxiliary apparatus.

In known systems, such for example as in the above mentioned EP-A 0061317, the piston rod which controls the mobile piece carrying the sample taking needle itself serves as guide for this mobile piece, in association with another guide, and the force exerted is not centered on this mobile piece and is cantilevered, that is to say that the movement of the needle under the action of this offcentered force may be disturbed by the play which said piece may take on, possibly causing jamming thereof. Furthermore, the system thus described uses an appreciable number of complicated profile pieces, taking up a not inconsiderable space to the detriment of mounting the assembly and its cost price.

The invention consequently provides a stopper piercing assembly for automatically taking liquid from a bottle and more particularly blood from a tube, which answers these requirements and which avoids the drawbacks experienced by known systems.

SUMMARY OF THE INVENTION

Thus, the invention provides a device for automatically taking liquid from a bottle presented upside down opposite a sample taking needle intended to pierce the stopper of the bottle and penetrate into the liquid, including a mobile support for storing a plurality of bottles allowing a bottle to be placed in a correct position with respect to a stopper piercing assembly, said assembly including a mobile block serving as support for a sample taking needle, which moves under the action of an actuating cylinder, a rinsing receptacle being fixedly mounted through which the needle passes, in which device said mobile block slides on two fixed guide columns between which the sample taking needle moves vertically under the action of an actuating cylinder with horizontal movement transmission and in which a fixed spacer is mounted bearing on the two columns, at their upper part, and serves as support for the rinsing receptacle.

According to another feature of the invention, at least one bell-crank linkage of substantially triangular shape forms the member for transmitting the movement of the mobile rod of the actuating cylinder to the mobile block and is pivotally mounted on a fixed pin itself mounted on a bracket secured to a support plate carrying the guide columns, each bell crank linkage cooperating with the mobile block through a spur formed by a bearing in an oval recess provided on the side wall of the mobile block. We thus have transmission of a horizontal movement of the actuating cylinder to a vertical movement of the mobile block.

The device of the invention has the advantage of requiring reduced space which avoids having to increase the height of the automatic device so as to be able to house it or else of encumbering the rear face of the means holding the samples. Furthermore, the device of the invention is easy to machine and mount, so of a low cost price, and it operates reliably since driving of the mobile element is provided without cantilevering nor with lateral force.

BRIEF DESCRIPTION OF THE DRAWINGS

Other particular features and advantages of the invention will be clear from reading the following description of one embodiment given by way of example, with reference to the accompanying drawings which show:

FIG. 1, a schematical elevational view of the piercing assembly in the rest position;

FIGS. 2 and 3, plane views through II—II and III—III of FIG. 1;

FIG. 4 a schematical view of the piercing assembly in the sample taking position; and FIG. 5, a sectional view through line V—V of FIG. 1.

DESCRIPTION OF THE PREFERRED EMBODIMENT

The automatic sample taking device includes essentially a rotary dispenser 1 for sample taking tubes or bottles 2, disposed above a piercing assembly mounted on a base 4. A selected tube 2 is automatically positioned as shown in a vertical liquid sample taking position and upside down (i.e., inverted), the stopper 3 being at the low part. On a support plate 5 fixed to base 4 are mounted a bracket 9 and two vertical guide columns 6. Bracket 9 is provided with a horizontal pin 7 by means of which two bell crank linkages 8 of substantially triangular shapes are mounted on each side of the bracket and each apex of which receives a pivot and/or hinge pin. These bell crank linkages form the members for transmitting movement between a drive means formed by an actuating cylinder 12 and a sample taking needle 21 the vertical guide columns 6 being located on opposite sides of a vertical path of travel of the needle. There is thus transmission of a horizontal movement of the cylinder to a vertical movement of the mobile block. To ensure this function, the upper ends of each bell crank linkage 8 are journalled by a horizontal pin 19 to a bearing 10 screwed on the mobile rod or piston 11 of a pneumatic cylinder 12. Said cylinder, fed with fluid through flexible pipes 13, is hingedly mounted to a stirrup 14 itself secured to base 4. The lower ends of each bell crank linkage 8 are provided with bearings 15 which cooperate with oval recesses 16 in the opposite side walls of a mobile block 17. This mobile block is provided with two vertical openings through which it is fitted on the guide column 6, ball guides 18 being provided on the mobile block for facilitating sliding of the block along the columns. A mobile block 17 has centrally a cavity 28 in which is positioned the lower end of a stop 20 for a sample taking needle 21, stop 20 being brazed to the needle 21 and said cavity being extended by a well 32 which opens at the lower part of the mobile block. A needle locking sleeve 22 fitted above stop 20 is locked in position by a screw 30 which passes through the mobile block 17. The lower end of needle 21 projects from the bottom of cavity 28 into well 32 which passes through the mobile block, and is connected to a flexible pipe 31 which extends under said block and which allows transfer of the fluid sample taken.

The top part of the guide column 6 is fixed to a fixed spacer 23, secured thereto, which is in the form of a rectangular plate formed with a central orifice 24. Orifice 24 opens onto the upper face of the spacer in the middle of a piece 25 forming a guide for the sample taking needle, which guide is held in position at the upper part of the spacer. Spacer 23 is fixed to column 6 by means of point screws 29. A rinsing receptacle 26, a lower orifice of which corresponds to orifice 24, is fixed above spacer 23 and is sealingly traversed by the sample taking needle 21. Receptacle 26 is provided on the side with a supply and drain pipe 27.

During a sample taking operation, one of tubes 2 carried by the rotary dispenser is selected by the operator who, for example, sets its reference number on an indexing keyboard. The dispenser rotates until the tube is in the position shown in FIG. 1. During such rotation, rod 11 of the pneumatic cylinder 12 is extended and the mobile block 17 is at rest bearing on the support plate 5. The upper end of needle 21 is at the level of the rinsing receptacle 26. When tube 2 is immobilized in the vertical position, the piercing assembly is automatically set in operation as shown in FIG. 4. The rod 11 of cylinder 12 retracts and through bearing 10 causes the bell crank linkages 8 to pivot about pin 7. Through bearings 15 cooperating with recesses 16, this pivoting movement causes lifting of the mobile block 17 until it comes close to spacer 23. During this rising movement, the bearing 15, because of the free movement of the end of the bell crank linkages 8, moves inside recess 16 transversally to column 6. The mobile block slides along the guide column 6, this movement being facilitated by the ball guides 18.

The point of application of the force for lifting the mobile block being situated in the middle centrally of this latter, there is no cantilever nor lateral force, thus the block may slide easily on the guide columns, without any risk of jamming.

The needle 21 fast with the mobile block also rises through orifice 24 and guide 25. It passes through stopper 3 and its end, which is inside the sample tube 2, allows the blood sample to be taken which is pumped by passing through the needle and the flexible pipe 31. Then the piercing assembly comes back to its initial position. The upper end of syringe 21 is rinsed in receptacle 26 which is fed with rinsing fluid through pipe 27.

The whole of the above described apparatus occupies a reduced space, which avoids increasing the total height of the automatic device or encumbering the rear face of the means holding the samples, and it only requires a few parts which are simple to produce and mount, and therefore inexpensive. All these programmed operations are automatically and rapidly carried out so as to be able to take a succession of samples at a good rate. Venting to the atmosphere is also provided during sample taking for compensating the volume removed and avoiding a depression in the tube.

We claim:

1. In a device for automatically taking liquid from a bottle presented upside down opposite a sample taking needle intended to pierce the stopper of the bottle and penetrate into the liquid, including a mobile support for storing a plurality of bottles and moving a bottle into a preselected position with respect to a stopper piercing assembly, said assembly including a mobile block serving as a support for the sample taking needle and being movable under the action of an actuating cylinder, with the sample taking needle being essentially centered on the mobile block, and a rinsing receptacle which is fixedly mounted and through which the needle passes, wherein said mobile block slides on two fixed vertical guide columns between which the actuating cylinder is operatively connected to the mobile block essentially at the middle of the block, and between which the sample taking needle moves vertically by transmission of the action of the actuating cylinder by transmission of a horizontal movement produced therewith, and wherein a fixed spacer is mounted on the two columns at their upper ends and serves as a support for the rinsing receptacle.

2. The sample taking device as claimed in claim 1, wherein said mobile block has at its center a cavity in which is positioned a lower end of a stop of the sample taking needle, this cavity being extended by a well which opens at the lower part of the mobile block.

3. The sample taking device as claimed in claim 2, wherein said stop is a positioning stop integrally secured to the needle and placed at the bottom of the cavity and wherein a needle locking sleeve is provided above the stop.

4. The sample taking device as claimed in claim 1, wherein at least one bell-crank linkage provides the transmission of the horizontal movement produced with the cylinder to the vertical movement of the mobile block and is pivotally mounted on a fixed pin.

5. The sample taking device as claimed in claim 4, wherein the bell crank linkage has a substantially triangular shape, each apex of which receives a pivot pin.

6. The sample taking device as claimed in claim 4, wherein said fixed pin is mounted on a bracket secured to a support plate carrying the guide columns.

7. The sample taking device as claimed in claim 4, wherein each bell crank linkage cooperates with the mobile block through a bearing in an oval recess provided on an adjacent side wall of the mobile block.

8. The sample taking device as claimed in claim 4, wherein each b crank linkage is journalled to a bearing screwed on a mobile rod of the actuating cylinder.

9. The sample taking device as claimed in claim 1, wherein said rinsing receptacle is provided with a lower orifice which corresponds to an orifice provided in the spacer for passage of the sample taking needle.

10. The sample taking device as claimed in claim 1, wherein said rinsing receptacle is fixed to the spacer above a piece forming a guide for the sample taking needle.

11. A device for automatically taking liquid from bottles each having a stopper in one end, wherein each of the bottles is automatically moved into a sample taking position with the bottle inverted, which comprises:

vertically movable block means for supporting an elongated vertically extending sample taking needle beneath and in essentially vertical alignment with the sample taking position;

a pair of spaced vertically extending guide means located on opposite sides of a path of travel of the elongated sample taking needle toward and away from the sample taking position, for guiding the support block means and the needle for vertical movement in a sample taking operation;

rinsing receptacle means fixedly mounted between the pair of spaced vertically extending guide means and through which the sample taking needle passes, for rinsing the needle after the sample taking operation;

actuating cylinder means movable horizontally for moving the support block means and the sample taking needle vertically upward toward one of the bottles in the sample taking position so that the needle pierces the stopper in the bottle, and for moving the support block means and the sample taking needle vertically downward after the sample taking operation; and means for connecting the actuating cylinder means to the support block means essentially centrally between the pair of spaced vertically extending guide means and in substantially vertical alignment with the sample taking needle to prevent jamming during the sample taking operation.

12. The device as recited in claim 11, which further comprises a spacer member extending between upper ends of the pair of spaced vertically extending guide means, the rinsing receptacle means being supported on the spacer member.

13. The device as recited in claim 11, wherein the support block means includes a central cavity, a stop on the sample taking needle is positioned in the cavity, and a sample withdrawing line is connected to the cavity through a lower part of the support block means.

14. The device as claimed in claim 13, wherein the sample taking needle is secured to the support block means by a sleeve fixedly mounted on the needle and to the support block means above the stop.

15. The device as recited in claim 11, wherein the connecting means includes at least one bell-crank member having opposite ends pivotably connected to the actuating cylinder means and the support block means, respectively, and means for supporting the bell-crank member for pivotable movement intermediate its opposite ends.

16. The device as claimed in claim 15, wherein the at least one bell-crank member is connected to the support block means by a member received in a horizontally extending oval recess in the support block means.

* * * * *